US006695805B1

(12) United States Patent
Sun et al.

(10) Patent No.: US 6,695,805 B1
(45) Date of Patent: *Feb. 24, 2004

(54) SYSTEMS AND METHODS FOR REMOVING FREE AND ENTRAINED CONTAMINANTS IN PLASMA

(75) Inventors: Chong-Son Sun, Lake Forest, IL (US); John Chapman, Lake Villa, IL (US); Daniel F Bischof, McHenry, IL (US); Robert E Herman, Lindenhurst, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/073,230

(22) Filed: May 5, 1998

Related U.S. Application Data

(62) Division of application No. 08/574,741, filed on Dec. 19, 1995, now Pat. No. 5,935,092, which is a continuation-in-part of application No. 08/289,175, filed on Aug. 11, 1994, now Pat. No. 5,536,238, which is a continuation of application No. 08/215,968, filed on Mar. 17, 1994, now abandoned, which is a continuation of application No. 08/055,915, filed on Apr. 29, 1993, now abandoned, which is a continuation of application No. 07/630,864, filed on Dec. 20, 1990, now abandoned.

(51) Int. Cl.[7] .......................... A61M 37/00; A61M 1/36; A01N 1/02; A61K 35/16
(52) U.S. Cl. .................... 604/6.09; 604/4.01; 604/6.03; 422/44; 435/2; 424/530; 424/532; 210/767; 210/496
(58) Field of Search ................................. 604/4–6, 4.01, 604/5.01, 5.02, 5.04, 6.03–6.04, 6.08, 7, 6.15–6.16, 20; 422/44, 56, 101–102; 210/767, 748, 435, 437, 488–90, 500.1, 500.21, 501, 496; 435/2; 424/529–34; 250/492.1, 500 R, 494.1, 496.1, 306–308

(56) References Cited

U.S. PATENT DOCUMENTS

| 3,876,738 A | 4/1975 | Marinaccion et al. |
|---|---|---|
| 4,025,618 A | 5/1977 | Garber et al. |
| 4,246,107 A | 1/1981 | Takenaka et al. |
| 4,340,479 A | 7/1982 | Pall |

(List continued on next page.)

FOREIGN PATENT DOCUMENTS

EP 0 500 472 A2 8/1992

OTHER PUBLICATIONS

Friedman and Stromberg, "Viral inactivation and reduction in cellular blood products", Transfusion Hemobiology, Jan. 1993; 36(1):83–91.*

Primary Examiner—Patricia Bianco
(74) Attorney, Agent, or Firm—Daniel D. Ryan; Michael C. Mayo

(57) ABSTRACT

Systems and methods treat plasma carrying contaminants and leukocytes that are capable of entraining contaminants. The systems and methods separate leukocytes from the plasma by filtration, thereby removing contaminants entrained within leukocytes. The systems and methods also add to the plasma a photoactive material and emit radiation at a selected wavelength into the plasma to activate the photoactive material and thereby eradicate the contaminant that is free of entrainment by leukocytes.

8 Claims, 5 Drawing Sheets

U.S. PATENT DOCUMENTS

| | | |
|---|---|---|
| 4,473,474 A | 9/1984 | Ostreicher et al. |
| 4,613,322 A * | 9/1986 | Edelson .......................... 604/6 |
| 4,673,504 A | 6/1987 | Ostreicher et al. |
| 4,701,267 A | 10/1987 | Watanabe et al. |
| 4,708,803 A | 11/1987 | Ostreicher et al. |
| 4,711,793 A | 12/1987 | Ostreicher et al. |
| 4,900,449 A | 2/1990 | Kraus et al. |
| 4,915,683 A | 4/1990 | Sieber |
| 4,925,572 A * | 5/1990 | Pall .......................... 210/767 |
| 4,950,665 A * | 8/1990 | Floyd ..................... 514/222.8 |
| 4,964,990 A | 10/1990 | Kraus et al. |
| 4,985,153 A | 1/1991 | Kuroda et al. |
| 5,023,052 A | 6/1991 | Nagatoma et al. |
| 5,076,935 A | 12/1991 | Kraus et al. |
| 5,089,146 A | 2/1992 | Carmen et al. |
| 5,100,564 A | 3/1992 | Pall et al. |
| 5,102,407 A | 4/1992 | Carmen et al. |
| 5,108,607 A | 4/1992 | Kraus et al. |
| 5,229,012 A | 7/1993 | Pall et al. |
| 5,252,222 A | 10/1993 | Matkovich et al. |
| 5,288,403 A | 2/1994 | Ohno |
| 5,298,165 A * | 3/1994 | Oka et al. |
| 5,300,019 A | 4/1994 | Bischof et al. |
| 5,387,187 A | 2/1995 | Fell et al. |
| 5,399,268 A | 3/1995 | Pall et al. |
| 5,403,272 A | 4/1995 | Deniega et al. |
| 5,423,989 A | 6/1995 | Allen et al. |
| 5,476,587 A | 12/1995 | Kuroki et al. |
| 5,494,592 A | 2/1996 | Latham, Jr. et al. |
| 5,498,336 A | 3/1996 | Katsurada et al. |
| 5,498,340 A | 3/1996 | Granger et al. |
| 5,501,795 A | 3/1996 | Pall et al. |
| 5,512,187 A | 4/1996 | Buchholz et al. |
| 5,536,238 A * | 7/1996 | Bischof |
| 5,536,413 A | 7/1996 | Bormann et al. |
| 5,545,339 A | 8/1996 | Bormann et al. |
| 5,545,516 A | 8/1996 | Wagner |
| 5,549,834 A | 8/1996 | Brown |
| 5,591,337 A | 1/1997 | Lynn et al. |
| 5,601,727 A | 2/1997 | Bormann et al. |
| 5,607,579 A | 3/1997 | Latham, Jr. et al. |
| 5,639,376 A | 6/1997 | Lee et al. |
| 5,660,731 A | 8/1997 | Piechocki et al. |
| 5,868,695 A * | 2/1999 | Wolf, Jr. et al. |
| 5,935,092 A * | 8/1999 | Sun et al. |
| 6,100,290 A * | 8/2000 | Levy et al. |
| 6,190,855 B1 * | 2/2001 | Herman et al. |

* cited by examiner

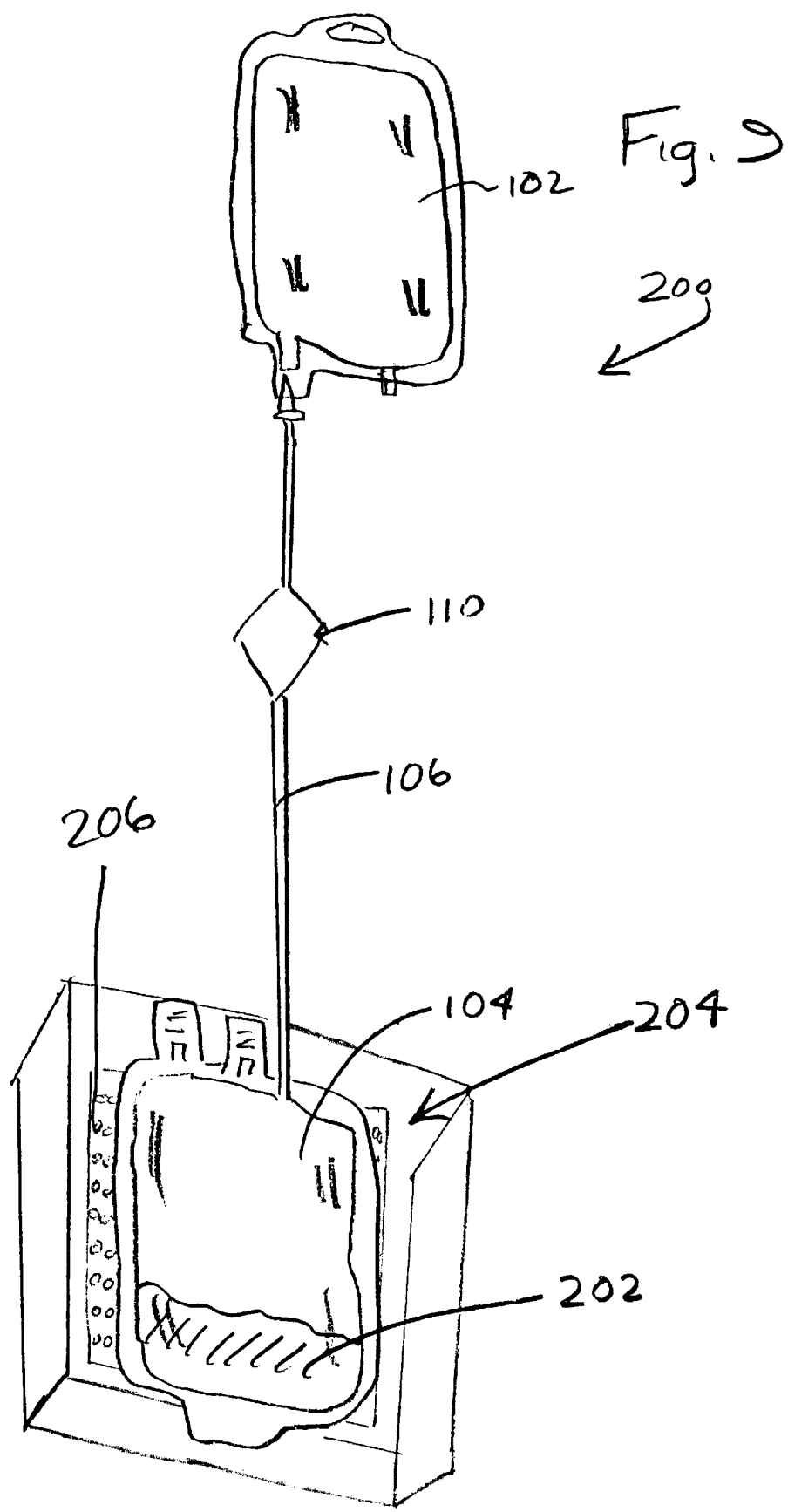

SYSTEMS AND METHODS FOR REMOVING FREE AND ENTRAINED CONTAMINANTS IN PLASMA

RELATED APPLICATION

This application is a division of copending application Ser. No. 08/574,741, filed Dec. 19, 1995 (now U.S. Pat. No. 5,935,092), which is a continuation in-part of U.S. patent application Ser. No. 08/289,175, filed Aug. 11, 1994 and entitled "Systems and Methods for Simultaneously Removing Free and Entrained Contaminants in Fluids Like Blood Using Photoactive Therapy and Cellular Separation Techniques" (now U.S. Pat. No. 5,536,238), which is a continuation of U.S. patent application Ser. No. 08/215,968, filed Mar. 17, 1994 (Abandoned), which is a continuation of U.S. application Ser. No. 08/055,915, filed Apr. 29, 1993 (Abandoned), which is itself a continuation of U.S. application Ser. No. 07/630,864, filed Dec. 20, 1990 (Abandoned).

FIELD OF THE INVENTION

The invention generally relates to the eradication of contaminants using photodynamic therapy. The invention also generally relates to the processing of whole blood and its components for storage and transfusion. In a more specific sense, the invention relates to the extracorporeal treatment of collected whole blood and its components with photoactive materials to eradicate viruses and other pathogenic contaminants.

BACKGROUND OF THE INVENTION

With the coming of blood component therapy, most whole blood collected today is separated into its clinically proven components for storage and administration. The clinically proven components of whole blood include red blood cells, used to treat chronic anemia; platelet-poor plasma, from which Clotting Factor VIII-rich cryoprecipitate can be obtained for the treatment of hemophilia; and concentrations of platelets, used to control thrombocytopenic bleeding.

It is well known that blood can carry infectious agents like hepatitis-B virus; the human immunodeficiency (AIDS) virus; the Herpes virus; and the influenza virus. To avoid the transmission of these infectious agents during blood transfusions, donors of blood are routinely screened and also undergo serologic testing to detect the presence of these agents. Still, it is difficult to always assure that these infectious agents are detected.

The use of photodynamic therapy has been suggested as a way to eradicate infectious agents from collected blood and its components. See Matthews et al, "Photodynamic Therapy of Viral Contaminants With Potential for Blood Bank Applications," *Transfusion*, 28(1), pp. 81–83 (1988). Various extracorporeal systems have been proposed that use photodynamic therapy to treat blood prior to storage and transfusion. See, for example, Edelson U.S. Pat. Nos. 4,613,322 and 4,684,521; Troutner et al U.S. Pat. No. 4,708,715; Wiesehahn et al U.S. Pat. No. 4,727,027; Sieber U.S. Pat. Nos. 4,775,625 and 4,915,683; and Judy et al U.S. Pat. No. 4,878,891.

To date, there has been a general lack of success in economically adapting the benefits of photodynamic therapy to the demands of the blood banking industry. One reason for this is that not all biological contaminants are carried free within the blood where they can be readily coupled to photoactive agents. Some biological contaminants are entrained on or within white blood cells out of the reach of photoactive agents.

The extracorporeal systems proposed to date can eradicate only contaminants that are carried free within the blood. Prior systems have not provided a device that can remove both free and entrained biological contaminants from a fluid in a single pass through a single treatment zone.

For this and other reasons, the promise of photodynamic therapy in treating the nation's banked blood supply has gone largely unfulfilled.

SUMMARY OF THE INVENTION

The invention provides improved systems and methods for treating plasma to remove contaminants such as leukocytes and adventitious viral agents, which can be carried free within the plasma or entrained within the leukocytes in the plasma.

One aspect of the invention treats fresh frozen plasma by thawing the plasma and filtering the thawed plasma to remove leukocytes and thereby remove viral agents entrained in the leukocytes.

In a preferred embodiment, the systems and methods add a photoactive material to the thawed plasma. The emission of radiation at a selected wavelength into the thawed plasma activates the photoactive material to eliminate viral agents that are carried free in the plasma.

Another aspect of the invention provides systems and methods for treating plasma carrying contaminants and leukocytes that are capable of entraining contaminants. The systems and methods separate leukocytes from the plasma by filtration, thereby removing contaminants entrained within leukocytes. The systems and methods also add to the plasma a photoactive material and emit radiation at a selected wavelength into the plasma to activate the photoactive material and thereby eradicate the contaminant that is free of entrainment by leukocytes.

In a preferred embodiment, the filter includes a prefilter layer that also removes aggregates larger than leukocytes from thawed plasma. The filter also includes, in a downstream flow direction from the prefilter, a material having pores sized to remove leukocytes from thawed plasma by exclusion.

In a preferred embodiment, the material comprises polyether sulfone forming two layers, with the pores of the first upstream layer being larger than the pores of the second downstream layer. In a preferred embodiment, the pores of the first layer are about 1.2 $\mu$m in size and the pores of the second layer are about 0.8 $\mu$m in size.

Other features and advantages of the invention will be pointed out in, or will be apparent from, the drawings, specification and claims that follow.

DESCRIPTION OF THE DRAWINGS

FIG. 9 is a system for treating plasma by filtering the plasma to remove leukocytes while adding a photactive agent to eliminate, upon exposure to radiation, viral agents carried free in the plasma.

Figure 1:
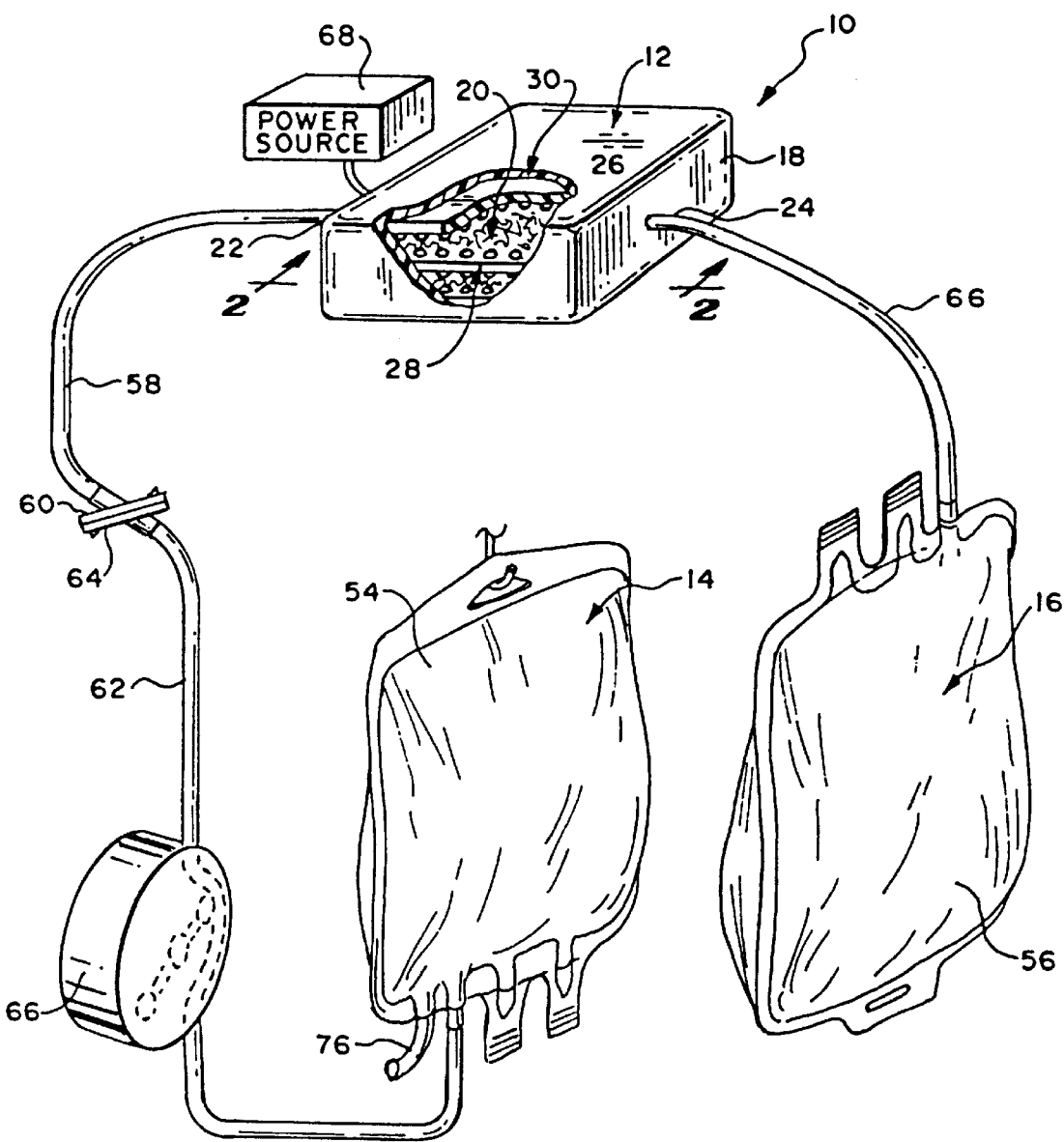
FIG. 1 is a perspective view, with portions broken away, of a system for treating a fluid carrying a contaminant that embodies the features of the invention.

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

FIG. 1 shows a system 10 for treating a fluid carrying contaminants that embodies the features of the invention. The contaminants are either carried free within the fluid or they are entrained on or within cellular matter that the fluid contains. According to the invention, the system 10 simultaneously removes both types of contaminants from the fluid within a single treatment zone.

The system 10 includes a treatment device 12 that receives the fluid from a source container 14 and conveys the fluid after treatment to a collection container 16.

The system 10 can treat various types of fluid. In the illustrated embodiment, the fluid comprises a suspension that includes at least one therapeutic component of whole human blood that is intended to be stored for transfusion. More specifically, the fluid consists of principally of red blood cells suspended in plasma. However, suspension also contains a quantity of white blood cells that are not be separated from the red blood cells using typical separation techniques. The fluid can also include an anticoagulant and, optionally, a storage medium for the blood component. Alternatively, the fluid can consist of platelets and a quantity of white blood cells suspended in plasma.

In the illustrated embodiment, the contaminant comprises a pathogenic virus typically carried in the blood. For example, the contaminant can consist of the hepatitis-B virus; the human immunodeficiency virus; the Herpes virus; or the influenza virus.

The white blood cells in the suspension are capable of ingesting or entraining such biological contaminants to remove them from the plasma. The contaminants that are not entrained by the white blood cells remain free in the plasma.

The treatment device 12 includes housing 18 that encloses an interior chamber 20. The chamber 20 has an inlet 22 for receiving the blood suspension from the source container 14 and an outlet 24 for discharging the blood suspension into the collection container 16.

The device 12 includes a first element 26 in the interior chamber 20 for removing the biological contaminants that are entrained within the white blood cell component. In the illustrated embodiment, the first element 26 serves to separate the cellular white blood cell component, and with it, the contaminant by filtration. However, it should be appreciated that the first element 26 can remove the cellular component by various centrifugal and non-centrifugal techniques, and not merely "filtration" in the technical sense. Separation of cellular matter can occur by absorption, columns, chemical, electrical, and electromagnetic means, and not just by filtration.

In the illustrated embodiment, the first element 26 includes conventional filtration medium for removing white blood cells from the blood. The filtration medium 26 can include cotton wool, cellulose acetate, or another synthetic fiber like polyester.

The filtration medium 26 can remove the white blood cells by conventional depth filtration techniques, or by conventional screen filtration techniques, or by surface specific filtration, by a combination of these techniques. In the illustrated embodiment, the filtration medium 26 comprises a bed of polyester fibers that entraps white blood cells using principally depth filtration.

The device 12 further includes a second element 28 in the interior chamber 20 for removing the biological contaminants that are carried free within the plasma, that is, outside the white blood cells. In the illustrated embodiment, the second element 28 employs photodynamic therapy to remove the free biological contaminants.

More particularly, the suspension in the source container 14 includes a photoactive material that has an affinity for the biological contaminant carried free within the plasma. The photoactive material is added to the blood suspension in the source container 14 in a preliminary step that will be described in greater detail later.

Due to its affinity for the contaminant, the photoactive material becomes bound to the contaminant carried free within the source container 14. The photoactive material is of a type that becomes active by exposure to radiation within a prescribed wavelength range. When activated by radiation, the material eradicates the contaminant.

Various types of photoactive materials can be used. In the illustrated embodiment, the photoactive compound comprises a family of light-activated drugs derived from benzoporphyrin. These derivatives are commonly referred as BPD's. BPD's are commercially available from Quadra Logic Technologies, Inc., Vancouver B.C., Canada.

BPD's, like other types of hematoporphyrin materials, have an affinity for the cell walls of many viral organisms that are carried in blood. They therefore bind or attach themselves to the biological cell wall of these organisms. When exposed to radiation, BPD's undergo an energy transfer process with oxygen, forming a singlet oxygen. When the singlet oxygen oxidizes, it kills the biological cells to which it has attached. BPD's are described in greater detail in Judy et al U.S. Pat. No. 4,878,891.

In the illustrated embodiment, the second element 28 emits radiation at a selected wavelength to activate the photoactive material bound to the biological contaminant. The second element 28 can be variously constructed. The drawings show three possible alternative embodiments.

Figure 2:
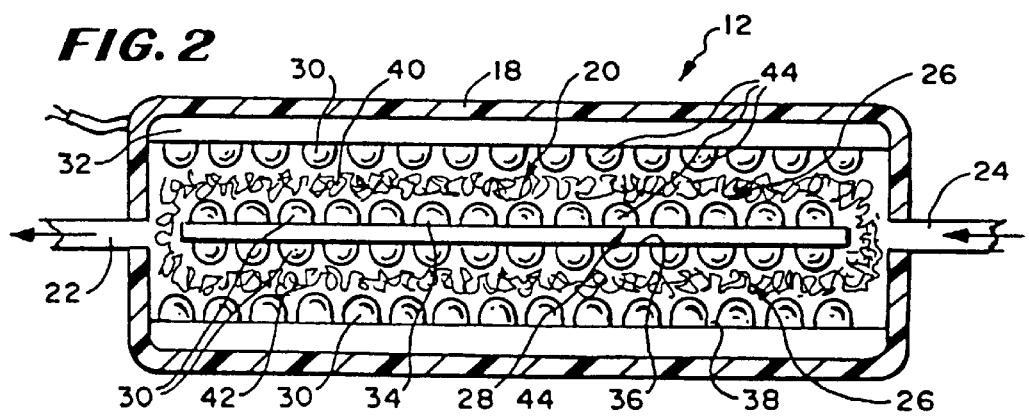
FIG. 2 is a section view of the treatment device associated with the system shown in FIG. 1, taken generally along line 2—2 in FIG. 1.

In the embodiment shown in FIGS. 1 and 2, the second element 28 includes one or more arrays 30 of radiation sources located along the flow path of the fluid between the inlet and outlet 22 and 24 of the chamber 20. The filtration medium 26 extends within these arrays 30. An external power element 68 is coupled to the arrays 30 for controlling their operation.

More particularly, the second element 28 includes four spaced apart banks 32, 34, 36, and 38 (see FIG. 2) of radiation sources located along the flow path of the fluid between the inlet and outlet 22 and 24 of the chamber 20. The banks 32 and 34 face each other, forming a first fluid branch path 40 between themselves. The other two banks 36 and 38 also face each other and between them form a second fluid branch path 42. In this arrangement, the filtration medium 26 occupies each branch path 40 and 42.

Each bank 32, 34, 36, and 38 comprises an arrangement of several discrete radiation sources 44. Each radiation source 44 is "discrete," meaning that each source 44 is a self-contained emitter of radiation that establishes its own zone of radiation. Being discrete, each source 44 also is capable of operation to emit a radiation independent of the emission of radiation by the other sources 44, if desired.

In the illustrated and preferred embodiment, each radiation source 44 takes the form of a photodiode. Various types of photodiodes can be selected, depending upon the fluid treated and the characteristics of the photoactive material used. In the illustrated embodiment, where the treated fluid contains red blood cells, all the photodiodes use transparent substrate aluminum gallium arsenide material (TS AlGaAs). Photodiodes of this type are commercially available from Hewlett-Packard Co. (Product designation HLMP-8150 15 Candella).

These photodiodes emit a band of radiation at a relatively narrow viewing angle of about 4 degrees. The prescribed band of radiation has a relatively precise wavelength displaying a red color having a peak wavelength of about 690 nm. Red blood cells are essentially transparent to radiation at this wavelength. The BPD's, however, are not. The BPD's absorb radiation in this wavelength to become activated.

If the blood suspension includes platelets, the photodiode would be selected to have a wavelength displaying a blue color having peak wavelength of about 425 nm. Platelets are essentially transparent to radiation at this wavelength.

In the illustrated embodiment, each discrete photodiode radiation source operates has a minimum intensity of about 8.0 cd (at 20 mA), a maximum intensity of about 36.0 cd (at 20 mA), and a typical intensity of about 15.0 cd (at 20 mA). Each photodiode operates at a low maximum forward voltage of about 2.4 V.

Figure 3:
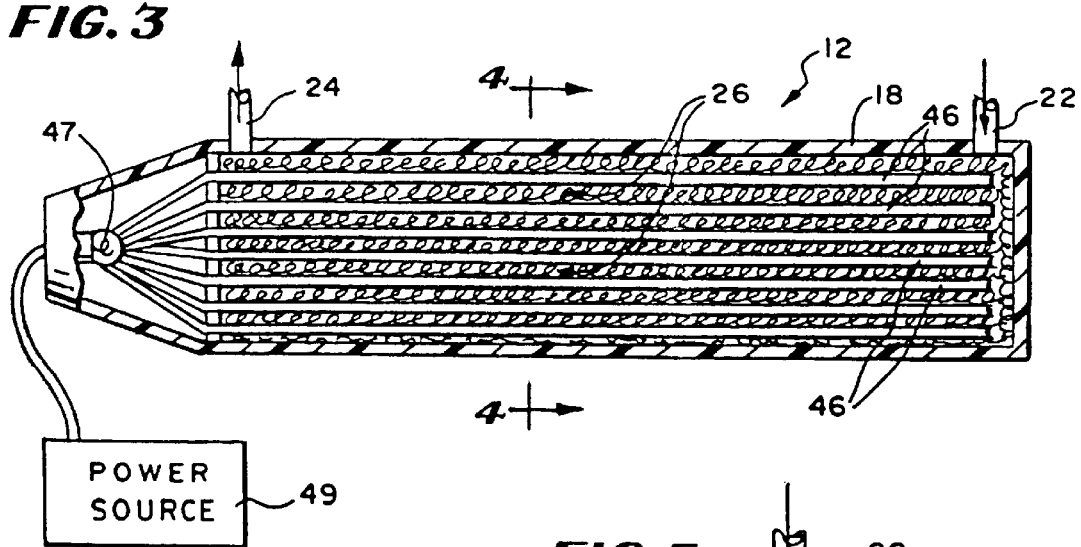
FIG. 3 is a section view of another embodiment of a treatment device that can be used in association with the system showing in FIG. 1.
Figure 4:
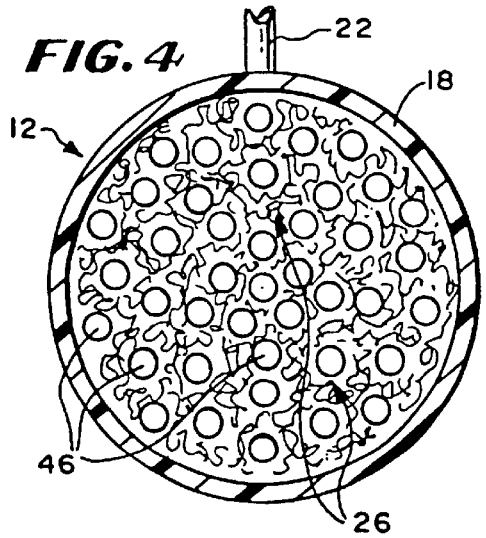
FIG. 4 is a view of the treatment device taken generally along line 4—4 in FIG. 3.

FIGS. 3 and 4 show an alternative embodiment. In this embodiment, at least one optical fiber 46 having a light emitting region 48 that extends within the filtration medium 26. As shown, an array of several optical fibers 46 extends within the filtration medium 26 (see FIG. 4), deriving their radiation from a single source 47. An external element 49 powers and controls the operation of the source 47.

In this arrangement, the cladding of each optical fiber 46 is removed in the region 48 where it extends into the filtration medium 26. The fibers 46 therefore emit radiation along this region 48.

Figure 5:
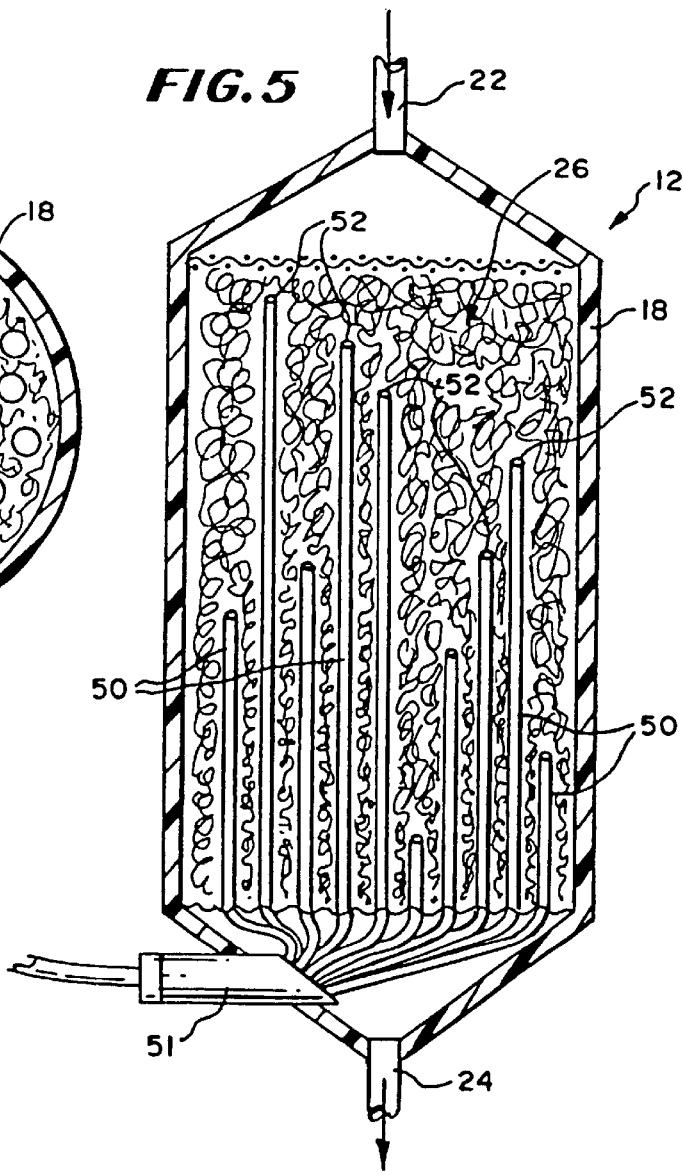
FIG. 5 is a section view of another embodiment of a treatment device that can be used in association with the system showing in FIG. 1.

FIG. 5 shows another alternative embodiment. In this embodiment, as in the embodiment shown in FIGS. 3 and 4, an array of several optical fibers 50 extends within the filtration medium. As in the FIGS. 3 and 4 arrangement, the fibers 50 derive their radiation from a single source 51. An external element (not shown) powers and controls the operation of the source 51 as in the FIGS. 3 and 4 embodiment.

Unlike the embodiment shown in FIGS. 3 and 4, the cladding of each optical fiber 50 remains in place, except at the tip end 52. The fibers 50 therefore emit radiation only from their tip ends 52. In this arrangement, the fibers 50 extend at different. lengths within the filtration medium 26 to assure a uniform dispersal of radiation along the fluid path.

In the illustrated embodiment, the source container 14 and the collection container 16 each takes the form of a bag (respectively 54 and 56) made of a flexible inert plastic material, like plasticized medical grade polyvinyl chloride.

Figure 6:
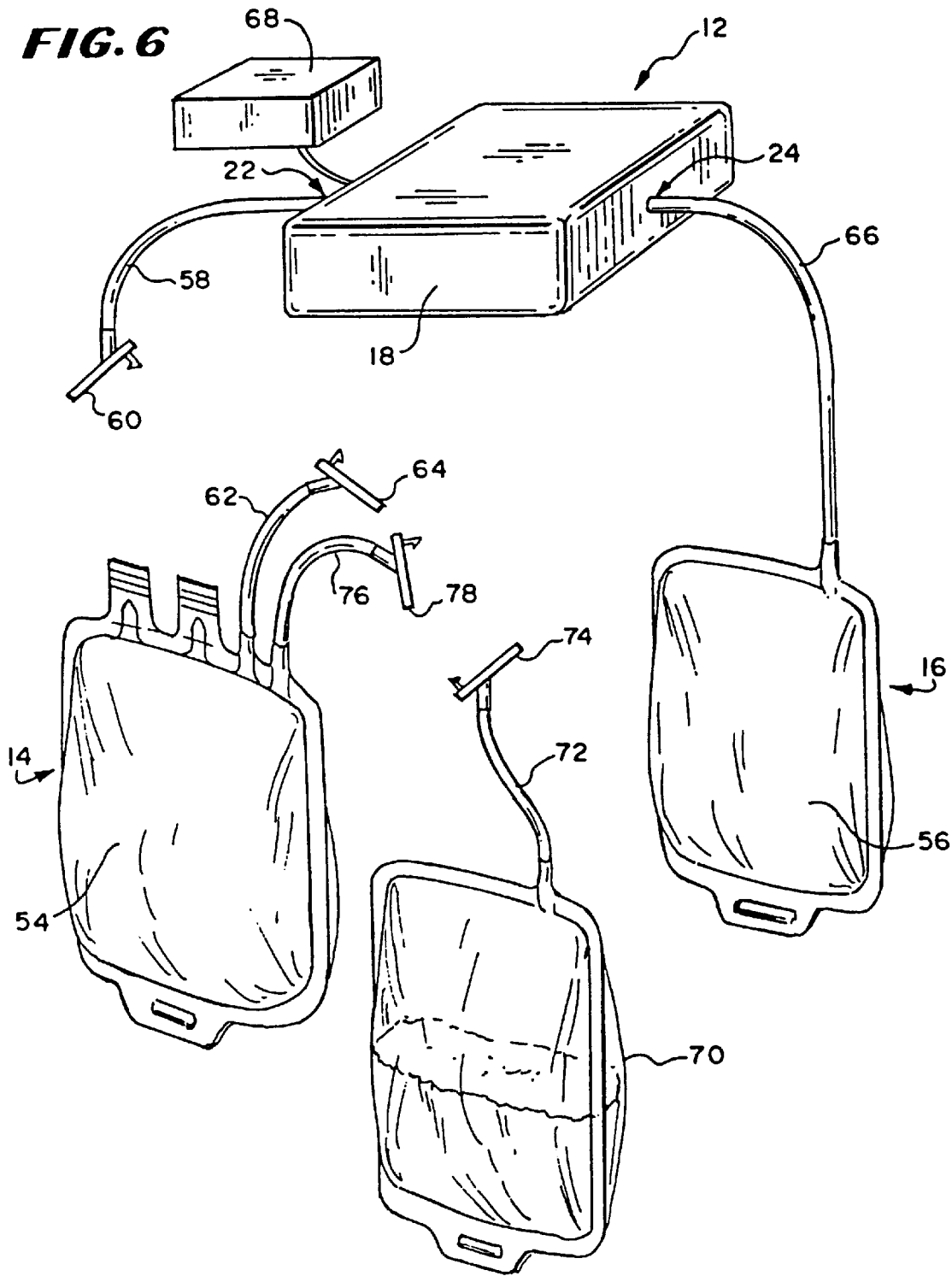
FIG. 6 is a perspective view of the component parts of the system shown in FIG. 1, with the component parts disassembled prior to use.

In the illustrated embodiment (see FIG. 6), the inlet 22 to the treatment device 12 includes a length of flexible inert plastic tubing 58. The tubing 58 terminates in a first connection device 60.

A length of flexible inert plastic tubing 62 also joins the source container 14. This tubing 62 includes a second connection device 64 that mates with the first connection device 60 to join the source container 14 to the inlet 22 of treatment device 12 (as FIG. 1 shows).

While various known connection devices may be used, in the illustrated embodiment, the devices 60 and 64 are preferable sterile connection devices like those shown in Granzow et al U.S. Pat. Nos. 4,157,723 and U.S. Pat. No. 4,265,280, which are incorporated herein by reference.

In use, a peristaltic pump 66 (see FIG. 1) conveys fluid through into the treatment device 12 at a predetermined flow rate.

The outlet 24 of the treatment device 12 also includes a length of flexible inert plastic tubing 66. The end of the tubing 66 joins the collection container 16. In an alternative arrangement (not shown), the tubing 66 could be normally separated into two lengths, like tubings 58 and 62, each having a sterile connection device to join the collection container 16 to the outlet 24 of the treatment device 12 prior to use.

In the illustrated embodiment (see FIG. 6), an auxiliary container 70 holds a solution containing the photoactive material. The auxiliary container 70 also includes a length of tubing 72 that carries with a third (preferably sterile) connection device 74. In this arrangement, the source container 14 also includes another length of tubing 76 that carries a fourth (preferably sterile) connection device 78. By joining the third and fourth sterile connection devices 74 and 78, the photoactive material can be conveyed from the auxiliary container 70 into the source container 14 for mixing with the fluid to be treated. The joined tubings 72 and 76 form a closed, internally sterile path for introducing the photoactive materially into the source container 14. Once the photoactive material has been transferred, the tubing 76 can be heat sealed closed downstream of the joined connection devices 74 and 78 (as FIG. 1 shows), and the auxiliary container 70 removed.

By using the sterile connection devices 60, 64, 74, and 78, the formed flow path comprises a closed, internally sterile path for conveying fluid from the source container 14, through the treatment chamber 20, and into the collection container 16.

After treatment, the tubing 66 can be heat sealed closed and the collection container 16 removed for storage.

In use, the device 12 can be used to treat a fluid carrying biological contaminants, including those biological contaminants that are entrained within a cellular component carried within the fluid.

In using the device 12, a photoactive material is added to the fluid. The photoactive material binds to the biological, contaminants that not entrained by the cellular component. Next, the fluid is conveyed into the device 12 along a predetermined path. As the fluid flows along the path within the device 12, the cellular component capable of entraining biological contaminants is removed by filtration from the fluid. At the same time, radiation is emitted at a selected wavelength into the fluid path within the device 12 to activate the photoactive material and thereby eradicate the contaminant that is not entrained within the cellular component.

Figure 7:
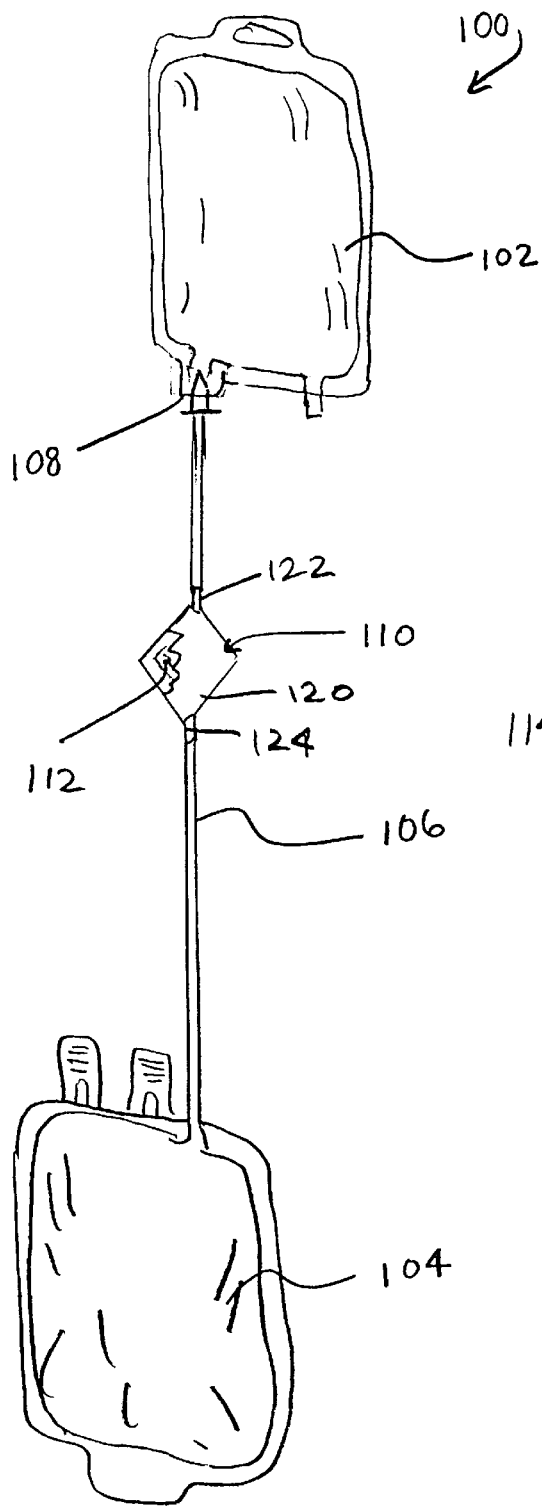
FIG. 7 is a system for treating plasma by filtering the plasma to remove leukocytes.

FIG. 7 shows a system 100 for treating human plasma prior to infusion or fractionation. The system includes a source container 102 containing plasma, which has been separated by centrifugation from whole blood. The source plasma can comprise stored frozen plasma that has been thawed in the source container 102.

The system 100 also includes a transfer container 106. A length of flexible tubing 106 is coupled at opposite ends to the source container 102 and the transfer container 104. In the illustrated embodiment, the tubing 106 is integrally connected to the transfer container 104 during manufacture. The transfer container 104-tubing 106 assembly is connected to the source container 102 during use by a conventional spike connector 108. Sterile connection devices shown in FIG. 6 can also be used.

The flexible tubing 106 includes an in line filter 110, which, in the illustrated embodiment, forms an integral part of the tubing 106. The filter 110 includes a medium 112 that removes leukocytes from plasma. Typically, fresh frozen human plasma can contain upward to $10^7$ leukocytes per unit. The filter 110 significantly reduces this amount, thereby reducing the likelihood of febrile and other reactions in recipients caused by the presence of leukocytes. The removal of leukocytes by the filter 110 also takes from the plasma intracellular viral contaminants that the leukocytes can carry.

Figure 8:
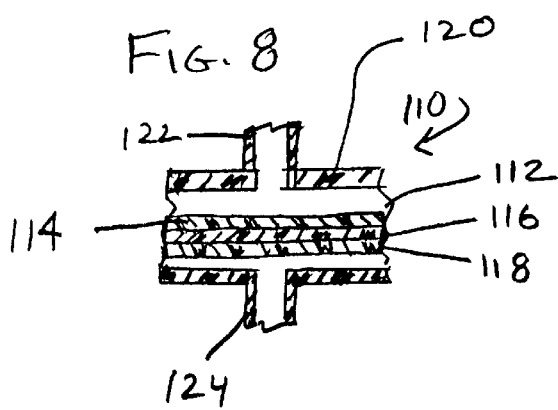
FIG. 8 is a side section view of the filter used in FIG. 7b to filter leukocytes from plasma.

In the illustrated and preferred embodiment (see FIG. 8), the filter medium 112 includes a prefilter mat layer 114 comprising USP Grade VI glass fiber or the equivalent. The purpose of the prefilter layer 114 is to remove fibrin clots and other large size aggregates from the plasma.

The filter medium 112 further includes downstream of the prefilter mat 114 one or more polymeric membrane filter layers 116, 118 with pore sizes selected to remove leukocytes by exclusion. Preferable, the pore size of the layers 116 and 118 decreases in the direction of flow. A preferred implementation includes a first layer 116 of polyether sulfone membrane having a pore size of about 1.2 µm and a second layer 118 of polyether sulfone membrane having a pore size of about 0.8 µm.

The prefilter layer 112 and membrane filter layers 116, 118 are preferably mounted within a common housing 120. An inlet 122 conveys plasma and leukocytes from the source container 102 into contact with the prefilter layer 112. An outlet 124 conveys leukocyte-reduced plasma from the membrane filter layers 116, 118 into the transfer container 104.

FIG. 9 shows a system 200 that combines inactivation of cell-free viruses (like HIV, VSV, and DHBV) in plasma with the removal of leukocytes-bound viruses (like HIV chronically infected H-9 cell lines) from the plasma using filtration.

The system 200 includes the source container 102, transfer container 104, tubing 106, and filter 110, as previously described in conjunction with FIG. 7. The system 200 further includes a photoactive material 202, which is added to the plasma, either before, during, or after passage through the filter 110. In the illustrated embodiment, the photoactive material 202 is carried in the transfer container 104 and is therefore mixed with the plasma after passage through the filter 110. The plasma and photactive material mixture in the transfer container 104 is exposed within a chamber 204 to light radiation, which inactivates certain viruses that may be carried in the plasma.

It should be appreciated that the photoactive material 202 can be added to the source container 102 from an auxiliary container (not shown), or into the tubing 106 through a Y-connector or drip chamber (also not shown), for mixture with the plasma before or during filtration.

In the,illustrated and preferred embodiment, the photoactive material 202 is methylene blue. The plasma (now leukocyte-reduced) and methylene blue solution is incubated in the transfer container 104 at ambient temperature for a period of time after the plasma is filtered. The transfer container solution is then placed within the chamber 204 that supplies a precise dose of either intense red (670 nm) light using an array of LED's 206 or one or more white fluorescent lights. The light activates the methylene blue to release singlet oxygen, which inactivates certain viruses in the plasma.

FIG. 9 shows the chamber 204 in diagrammatic form.

It should be appreciated that the photoinactivation process can occur within the source container 102 with the addition of photoactivation material before filtration. It should also be appreciated that the photo-inactivation process can occur within the filter 110, as previously described in connection with embodiment shown in FIG. 1.

The system 200 provides more reliability and ease of use than the removal of leukocytes from plasma by lysing using conventional freeze-thaw processes. The system 200 also provides greater removal of adventitious agents (i.e., viruses) than mere light inactivation (which does not remove intracellular agents) and/or bed-side filtering of plasma (which only removes fibrin clots, and not leukocytes).

Features and advantages of the invention are set forth in the following claims.

We claim:

1. A system for treating plasma after separation from whole blood comprising
   a source container holding plasma after separation from whole blood,
   tubing adapted to be coupled the source container to convey plasma from the source container,
   a filter in the tubing to separate leukocytes from plasma conveyed from the source container comprising a fibrous prefilter medium to remove aggregates from the plasma by adsorption, and, in a downstream flow direction from the fibrous prefilter medium, a downstream membrane filter medium having pores sized to remove leukocytes by exclusion, and
   means for adding a photoactive material to the plasma.

2. A system for treating plasma after separation from whole blood comprising
   a source container holding plasma after separation from whole blood,
   a transfer container,
   tubing adapted to be coupled the source container and the transfer container to convey plasma from the source container to the transfer container,
   a filter in the tubing to separate leukocytes from plasma conveyed from the source container comprising a fibrous prefilter medium to remove agregates from the plasma by adsorption and, in a downstream flow direction from the fibrous prefilter medium, a downstream membrane filter medium having pores sized to remove leukocytes by exclusion, and
   means for adding a photoactive material to the plasma in one of the source container and transfer container.

3. A system for treating plasma after separation from whole blood comprising a transfer container, a photoactive material in the transfer container, tubing coupled to the transfer container and adapted to be coupled a source container of plasma after separation from whole blood to convey plasma from the source container into the transfer container for mixing with the photactive material, and a filter in the tubing to separate leukocytes from plasma conveyed into the transfer container comprising a fibrous prefilter medium to remove aggregates from the plasma by adsorption and, in a downstream flow direction from the fibrous prefilter medium, a downstream membrane filter medium having pores sized to remove leukocytes by exclusion.

4. A system according to claim 1 or 2 or 3 wherein the photoactive material is methylene blue.

5. A system according to claim 1 or 2 and or 3 and further including a light source emitting radiation at a selected wavelength into the plasma to activate the photoactive material.

6. A system for treating plasma after separation from whole blood comprising a source container holding plasma after separation from whole blood, tubing adapted to be coupled the source container to convey plasma from the source container, a filter in the tubing to separate leukocytes from plasma conveyed from the source container comprising a fibrous prefilter medium to remove aggregates from the plasma by adsorption and, in a downstream flow direction from the fibrous prefilter medium, a downstream membrane filter medium having pores sized to remove leukocytes by exclusion, the downstream membrane filter medium including first and second membrane layers, the first membrane layer being located between the fibrous prefilter medium and the membrane second layer, the pores of the first membrane layer being larger than the pores of the second membrane layer, and means for adding a photoactive material to the plasma.

7. A system for treating plasma after separation from whole blood comprising source container holding plasma after separation from whole blood, a transfer container, tubing adapted to be coupled the source container and the transfer container to convey plasma from the source container to the transfer container, a filter in the tubing to separate leukocytes from plasma conveyed from the source container comprising a fibrous prefilter medium to remove aggregates from the plasma by adsorption and, in a downstream flow direction from the fibrous prefilter medium, a downstream membrane filter medium having pores sized to remove leukocytes by exclusion, the downstream membrane filter medium including first and second membrane layers, the first membrane layer being located between the fibrous prefilter medium and the second membrane layer, the pores of the first membrane layer being larger than the pores of the second membrane layer, and means for adding a photoactive material to the plasma in one of the source container and transfer container.

8. A system for treating plasma after separation from whole blood comprising transfer container, a photoactive material in the transfer container, tubing coupled to the transfer container and adapted to be coupled a source container of plasma after separation from whole blood to convey plasma from the source container into the transfer container for mixing with the photactive material, and a filter in the tubing to separate leukocytes from plasma conveyed into the transfer container comprising a fibrous prefilter medium to remove aggregates from the plasma by adsorption and, in a downstream flow direction from the fibrous prefilter medium, a downstream membrane filter medium having pores sized to remove leukocytes by exclusion, the downstream membrane filter medium including first and second membrane layers, the first membrane layer being located between the fibrous prefilter medium and the second membrane layer, the pores of the first membrane layer being larger than the pores of the second membrane layer.

\* \* \* \* \*